(12) United States Patent
Ahn et al.

(10) Patent No.: US 11,759,633 B2
(45) Date of Patent: Sep. 19, 2023

(54) NON-INVASIVE NEURAL ELECTRODE ASSEMBLY AND NEURAL ELECTRODE CONTROL SYSTEM USING SAME

(71) Applicants: KOREA UNIVERSITY RESEARCH AND BUSINESS FOUNDATION, Seoul (KR); KOREA INSTITUTE OF SCIENCE AND TECHNOLOGY, Seoul (KR)

(72) Inventors: Ki Hoon Ahn, Seoul (KR); Soo Hyun Lee, Seoul (KR)

(73) Assignees: Korea University Research and Business Foundation, Seoul (KR); Korea Institute of Science and Technology, Seoul (KR)

(*) Notice: Subject to any disclaimer, the term of this patent is extended or adjusted under 35 U.S.C. 154(b) by 0 days.

(21) Appl. No.: 16/771,626

(22) PCT Filed: Nov. 29, 2018

(86) PCT No.: PCT/KR2018/014965
§ 371 (c)(1),
(2) Date: Jun. 10, 2020

(87) PCT Pub. No.: WO2019/146901
PCT Pub. Date: Aug. 1, 2019

(65) Prior Publication Data
US 2020/0353247 A1    Nov. 12, 2020

(30) Foreign Application Priority Data
Jan. 29, 2018  (KR) .................. 10-2018-0010574

(51) Int. Cl.
*A61N 1/36*    (2006.01)
*A61B 5/00*    (2006.01)
(Continued)

(52) U.S. Cl.
CPC ........ *A61N 1/36007* (2013.01); *A61B 5/0002* (2013.01); *A61B 5/391* (2021.01);
(Continued)

(58) Field of Classification Search
CPC .............. A61N 1/36007; A61N 1/0524; A61N 1/3606; A61N 1/36135; A61N 1/37223;
(Continued)

(56) References Cited

U.S. PATENT DOCUMENTS 8,543,210 B2    9/2013  Sharma
9,872,983 B2 *  1/2018  Garfield .............. A61N 1/0521
(Continued)

FOREIGN PATENT DOCUMENTS

JP    H08506974 A    7/1996
JP    2017086802 A   5/2017
(Continued)

OTHER PUBLICATIONS

Jong Hwa Kim, "New strategies in the treatment of preterm delivery", Korean Journal of Obstetrics and Gynecology, vol. 48, No. 7, Jul. 2005, pp. 1605-1612.

*Primary Examiner* — Tammie K Marlen
(74) *Attorney, Agent, or Firm* — Rabin & Berdo, P.C.

(57) ABSTRACT

The present disclosure relates to neural electrode technology for measuring a biosignal of a human or applying a neural signal to the human, and a neural electrode assembly includes a body that is inserted into a uterus in a non-invasive manner, a recording neural electrode formed to measure a uterine contraction-evoked neural signal, the recording neural electrode being coupled to the body, and a stimulating neural electrode formed to stimulate a nerve entering the uterus to suppress the uterine contraction, the stimulating neural electrode being coupled to the body.

12 Claims, 4 Drawing Sheets

(51) Int. Cl.
*A61N 1/05* (2006.01)
*A61N 1/372* (2006.01)
*A61B 5/391* (2021.01)

(52) U.S. Cl.
CPC ......... *A61N 1/0524* (2013.01); *A61N 1/3606* (2013.01); *A61N 1/36135* (2013.01); *A61N 1/37223* (2013.01); *A61B 2560/0406* (2013.01)

(58) Field of Classification Search
CPC ............ A61N 1/36031; A61N 1/36034; A61B 5/391; A61B 5/0002; A61B 5/4836; A61B 5/6875; A61B 5/4356; A61B 5/0024; A61B 2560/0406; A61B 2562/16
See application file for complete search history.

(56) References Cited

U.S. PATENT DOCUMENTS

| | | |
|---|---|---|
| 2002/0010494 A1 | 1/2002 | Policker et al. |
| 2013/0053670 A1 | 2/2013 | Aina-Mumuney et al. |
| 2014/0296933 A1* | 10/2014 | Haessler ............ A61N 1/36007 607/138 |
| 2016/0235978 A1 | 8/2016 | Haessler |
| 2020/0086110 A1* | 3/2020 | Karsdon ............ A61N 1/37223 |

FOREIGN PATENT DOCUMENTS

| | | |
|---|---|---|
| KR | 1020040101190 A | 12/2004 |
| WO | 2004037083 A1 | 5/2004 |

* cited by examiner

NON-INVASIVE NEURAL ELECTRODE ASSEMBLY AND NEURAL ELECTRODE CONTROL SYSTEM USING SAME

TECHNICAL FIELD

The present disclosure relates to neural electrode technology for measuring a biosignal of a human or applying a neural signal to the human, and more particularly, to a non-invasive neural electrode assembly for diagnosis or suppression of preterm birth and a neural electrode control system using the same.

BACKGROUND ART

In general, obstetric examination involves detecting a fetal heartbeat using the principle of ultrasound to check the health and abnormality of an unborn baby through changes in the detected heartbeat. That is, a pregnant woman may have an ultrasonic test in a hospital, and through the test, periodically monitor the baby's condition.

However, recently, due to stressful working environments in social life and changes in social environments such as environmental pollution, there is an increase in preterm birth, i.e., a birth that occurs before the estimated due date. Accordingly, in addition to the test for measuring the fetal heartbeat, a test for assessing the risk level of preterm birth may be performed by measuring the degree of uterine contraction of the pregnant woman.

Main testing and diagnostic methods related to preterm birth include looking for changes in cervical canal through bimanual examination, testing amniotic fluid leaking through colposcopy and checking for amniocentesis through chorioamnionitis. In relation to preterm birth, medication therapy using uterine contraction suppressors (ritodrine, atosiban, magnesium, etc.) and antibiotics has been chiefly conducted.

On the other hand, the related literature presented below describes the mechanism involved in the induction of preterm birth, various causes of preterm birth and strategies to reduce preterm birth, but it is still a lack of clear solution to prevent and treat preterm birth.

RELATED LITERATURES

Non-Patent Literature (Non-Patent Literature 1) "New strategies in the treatment of preterm delivery", Jong Hwa Kim, Korean Society of Obstetrics and Gynecology, 2005

DISCLOSURE

Technical Problem

The present disclosure is designed to solve the problems with low accuracy and resultant doubtful diagnostic effectiveness of the existing tests for prediction of preterm birth, and overcome the effect limitation of medication therapy used for medical phenomena to prevent or treat preterm birth.

Technical Solution

To solve the above-described technical problem, a neural electrode assembly according to an embodiment of the present disclosure includes a body that is inserted into a uterus in a non-invasive manner, a recording neural electrode formed to measure a uterine contraction-evoked neural signal, the recording neural electrode being coupled to the body, and a stimulating neural electrode formed to stimulate a nerve entering the uterus to suppress the uterine contraction, the stimulating neural electrode being coupled to the body.

In the neural electrode assembly according to an embodiment, the recording neural electrode may be disposed around the cervix by the insertion of the body into the uterus, to continuously monitor the uterine contraction-evoked neural signal.

In the neural electrode assembly according to an embodiment, the stimulating neural electrode may stimulate the nerve entering the uterus to suppress the uterine contraction when the uterine contraction is detected through the recording neural electrode. Additionally, the stimulating neural electrode may apply, to the nerve entering the uterus, a nerve stimulation signal of sufficient intensity to stop or delay preterm birth, corresponding to the detected degree of uterine contraction.

In the neural electrode assembly according to an embodiment, the stimulating neural electrode may be disposed adjacent to uterosacral ligaments on both sides of the cervix by the insertion of the body into the uterus, to stimulate sympathetic nerves of the uterosacral ligaments to suppress the uterine contraction.

In the neural electrode assembly according to an embodiment, the body may include a biocompatible material, and may be inserted into the uterus in a non-invasive manner and structurally fixed adjacent to the cervix.

The neural electrode assembly according to an embodiment may further include a communication unit electrically connected to the recording neural electrode and the stimulating neural electrode to wirelessly transmit and receive a signal and a command, and the communication unit may transmit the neural signal measured through the recording neural electrode to a monitoring terminal, and receive a command for suppressing the uterine contraction from the monitoring terminal to control the stimulating neural electrode.

To solve the above-described technical problem, a neural electrode control system according to another embodiment of the present disclosure includes a neural electrode assembly that is inserted into a uterus in a non-invasive manner to measure a uterine contraction-evoked neural signal and stimulate a nerve entering the uterus to suppress the uterine contraction, and a monitoring terminal to receive the uterine contraction-evoked neural signal continuously measured through the neural electrode assembly, and when the uterine contraction is detected, transmit a command for suppressing the uterine contraction to the neural electrode assembly to induce the neural electrode assembly to stimulate the nerve entering the uterus.

In the neural electrode control system according to another embodiment, the neural electrode assembly may include a recording neural electrode disposed around the cervix by the insertion into the uterus, to continuously monitor the uterine contraction-evoked neural signal, and a stimulating neural electrode disposed adjacent to uterosacral ligaments on both sides of the cervix by the insertion into the uterus, to stimulate sympathetic nerves of the uterosacral ligaments to suppress the uterine contraction.

Advantageous Effects

The embodiments of the present disclosure predict or continuously monitor the signs of preterm birth by detecting uterine muscle contractions that are the physiological phenomenon appearing in the mechanism by which preterm birth is induced, and when a uterine contraction is anticipated based on the detected neural signal, automatically apply electrical stimulation to the nerve entering the uterus using the non-invasive neural electrode, to suppress or delay the uterine muscle contraction, thereby preventing preterm birth.

BEST MODE

Prior to the detailed description of the embodiments of the present disclosure, an introduction to difficulties occurring in the field of technology and endeavor to which the embodiments of the present disclosure pertain and ideas generated to solve the problems will be described below.

Figure 1:
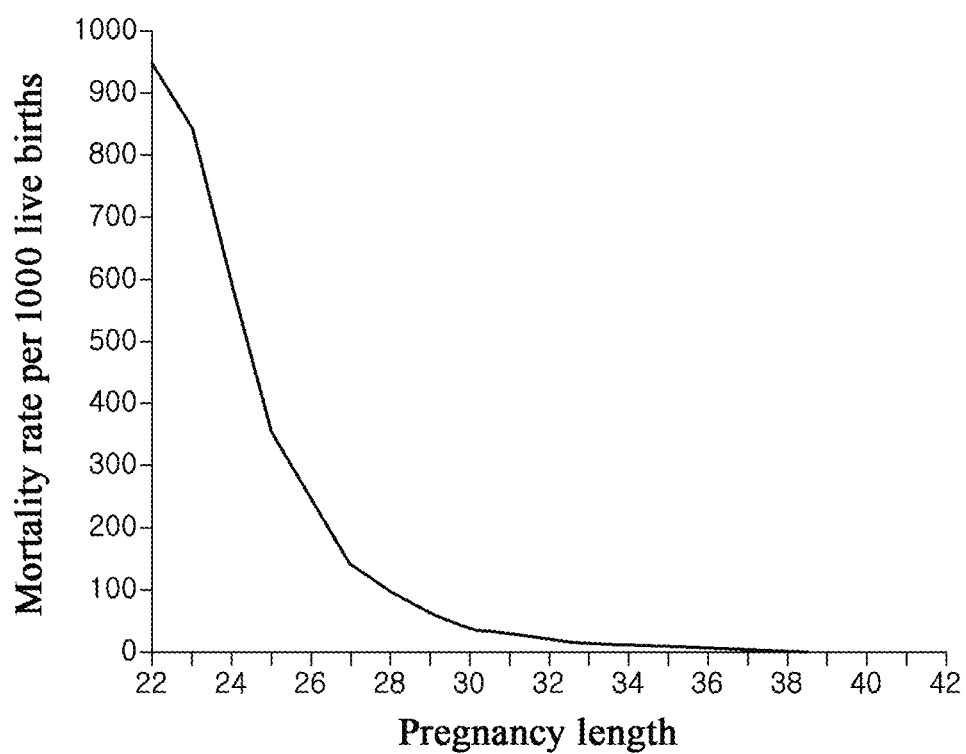
FIG. 1 is a graph showing changes in infant mortality rate as a function of pregnancy length.

FIG. 1 is a graph showing changes in infant mortality rate as a function of pregnancy length, and it can be seen that as the pregnancy length is shorter, the infant mortality rate extremely increases, whereas as babies are born closer to the expected due date past the risk of preterm birth, the infant mortality rate dramatically reduces. Currently, the preterm birth rate is about 10% of pregnancy, and is regarded as the most important cause of neonatal deaths that affect low birth rate and population reduction. Particularly, along with the trend in infant mortality rate, statistics representing the annual increase in the percentage of premature infants or low birth weights supports the need for preterm birth risk management.

It is known that the most significant cause of preterm birth (spontaneous preterm birth) is infection, and another cause is vascular disorders, decidual senescence, uterine overdistension, a decline in progesterone action, cervix diseases, breakdown of feto-maternal immune tolerance, and stress. As such, various causes are involved in the mechanism by which preterm birth is induced, but the last physiological phenomenon such as uterine muscle contraction and cervical dilatation is a common phenomenon.

Currently, to predict preterm birth, there are tests such as ultrasonic cervical length measurement, measurement of fetal fibronectin in vaginal secretions and amniotic fluid MMP-8 concentration measurement, but accuracy is not high, calling the diagnostic effectiveness into question. Additionally, not only prediction of preterm birth but also prevention and treatment of preterm birth is urgently needed, and the therapeutic effect of progesterone, antibiotics and preterm birth suppressors widely used in clinical applications is very low.

Meanwhile, under the recognition of the above-described problems, attention is directed to the fact that the autonomic nervous system richly innervates the organs located within the pelvis. The uterus, bladder, rectum and anus reside in the pelvis, and the autonomic nervous system including the sympathetic nerves and parasympathetic nerves controls the muscle contraction and relaxation and the functions of all the above organs, and particularly, stimulation of the parasympathetic nerves causes contraction of the organs in the pelvis, and stimulation of the sympathetic nerves causes relaxation of the organs in the pelvis. Accordingly, it is expected to ultimately treat spontaneous preterm birth by regulating the neural transmission in the pelvis based on the research about neurological regulation of the organs in the pelvis including the uterus.

Based on this technical understanding, the embodiments of the present disclosure propose technical means to effectively control uterine muscle contractions by figuring out which nerve is responsible for uterine muscle contractions or cervical dilatation among the organs in the pelvis, and stimulating the sympathetic nerves through the nerve. In addition to this, to minimize patients' discomfort, the embodiments of the present disclosure introduce a neural electrode of high biocompatibility that is inserted adjacent to the nerve entering the uterus in a non-invasive manner, and establish a control model to measure uterine contractions or stimulate the nerve entering the uterus through multiple types of neural electrodes. Particularly, these technical means are integrally formed into a single small device, thereby contributing to the early diagnosis and treatment of spontaneous preterm birth.

Hereinafter, the embodiments of present disclosure will be described in detail with reference to the accompanying drawings. However, in the following description and the accompanying drawings, a detailed description of known functions or elements that may render the key subject matter of the present disclosure ambiguous is omitted herein. In addition, the term 'comprises' when used in this specification, specifies the presence of stated elements, but does not preclude the presence or to addition of one or more other elements unless the context clearly indicates otherwise.

The terminology used herein is for the purpose of describing particular embodiments only and is not intended to be limiting of the present disclosure. As used herein, the singular forms include the plural forms as well, unless the context clearly indicates otherwise. It should be understood that the term "comprises" or "includes" when used in this specification, specifies the presence of stated features, integers, steps, operations, elements, components or groups thereof, but does not preclude the presence or addition of one or more other features, integers, steps, operations, elements, components or groups thereof.

Unless otherwise defined, all terms (including technical and scientific terms) used herein have the same meaning as commonly understood by one of ordinary skill in the art. The terms, such as those defined in commonly used dictionaries, should be interpreted as having a meaning that is consistent with their meaning in the context of the relevant art, and will not be interpreted in an idealized or overly formal sense unless expressly so defined herein.

Figure 2:
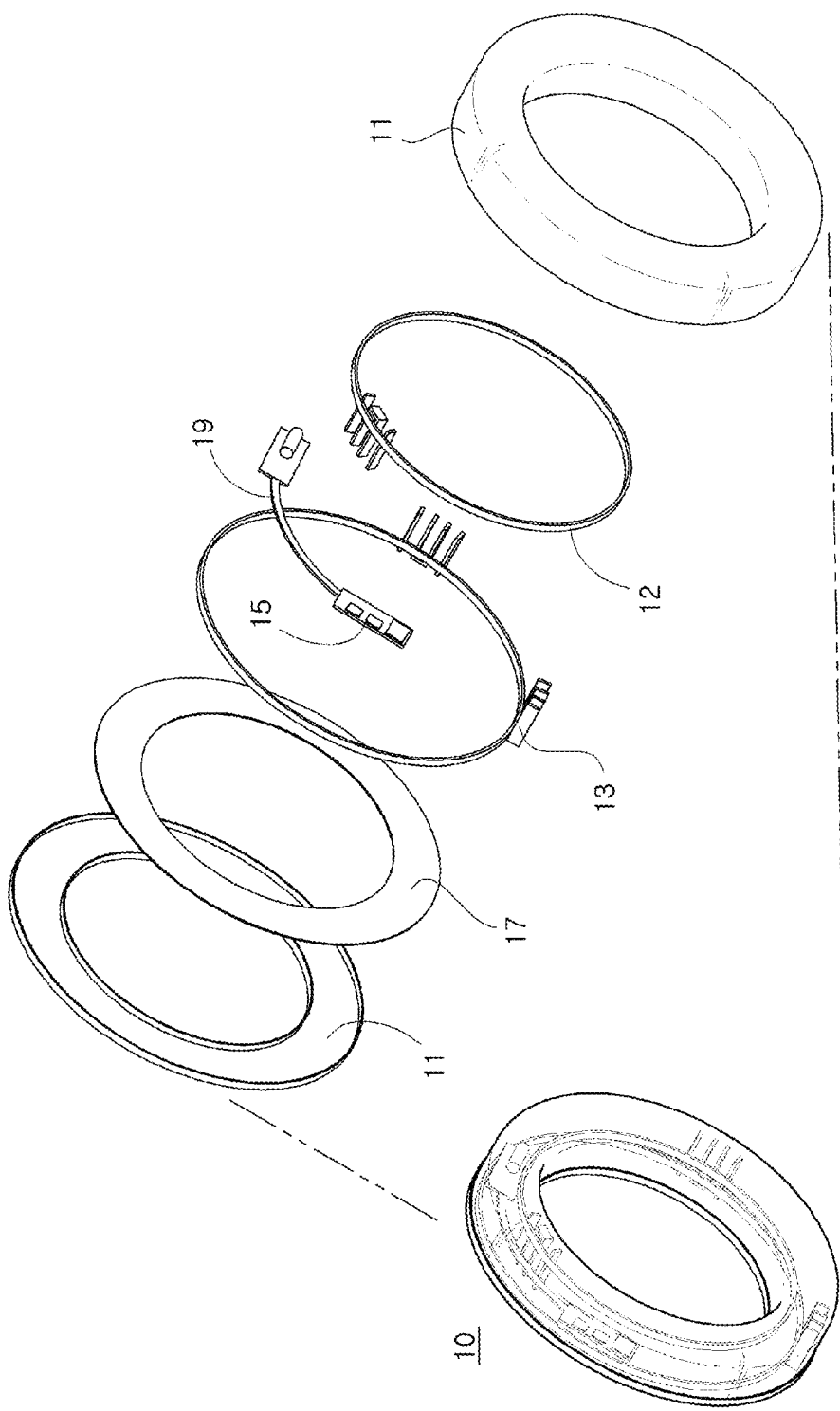
FIG. 2 is an exploded perspective view of a non-invasive neural electrode assembly according to an embodiment of the present disclosure.

FIG. 2 is an exploded perspective view of a non-invasive neural electrode assembly 10 according to an embodiment of the present disclosure.

A body is a component that is inserted into the uterus in a non-invasive manner, and may be covered with a cover 11 formed from a biocompatible material that is not harmful to the human body or may be coated with a biocompatible material on the surface. The body or the cover 11 may be made of any material that does not react to the human tissues, including various materials, for example, a biocompatible material such as ethylene vinyl acetate (EVA) copolymer, or a plastic material with high transparency and elasticity such as poly ethylene (PE), poly styrene (PS), poly ethylene terephthalate (PET), poly vinyl chloride (PVC), poly vinylidene chloride (PVDC), poly propylene (PP) and poly vinyl alcohol (PVA), thereby achieving good binding properties.

From the structural perspective, the body may be formed in the shape of a ring as shown in FIG. 2, but the body may be formed in a variety of other suitable shapes to be inserted into the uterus in a non-invasive manner, for example, a disk, a sphere, a cylinder, a rugby ball and a banana, and preferably, after inserted, may be structurally fixed to the inner walls of the uterus adjacent to the cervix.

A recording neural electrode 12 is formed to measure a uterine contraction-evoked neural signal, and is coupled to the body. The recording neural electrode 12 may be disposed around the cervix by the insertion of the body into the uterus, to continuously monitor the uterine contraction-evoked neural signal to predict and detect preterm labor.

A stimulating neural electrode 13 is formed to stimulate the nerve entering the uterus to suppress uterine contractions, and is coupled to the body. When a uterine contraction is detected through the recording neural electrode 12, the stimulating neural electrode 13 may stimulate the nerve entering the uterus to suppress the uterine contraction. Particularly, the stimulating neural electrode 13 may apply, to the nerve entering the uterus, a nerve stimulation signal with sufficient intensity to stop or delay preterm birth, corresponding to the detected degree of uterine contraction.

Additionally, the stimulating neural electrode 13 may be disposed adjacent to the uterosacral ligaments on both sides of the cervix by the insertion of the body into the uterus, to stimulate the nerve entering the uterus (primarily, the sympathetic nerves) of the uterosacral ligaments, and when a preterm labor occurs, apply appropriate electrical stimulation to suppress the uterine contraction.

Along with the foregoing components, the neural electrode assembly 10 of FIG. 2 includes a communication unit 17 to transmit the measured signal to a monitoring terminal located outside the human body, or receive a command for suppressing uterine contractions from the monitoring terminal. When considering the ring shaped body shown in FIG. 2, the communication unit 17 may be placed in the shape of a wireless coil along the inside of the body.

Further, the neural electrode assembly 10 may further include a power source 19 and a processing unit 15 to drive and control the neural electrode assembly 10. The power source 19 may supply necessary power to the neural electrode assembly 10, and the processing unit 15 may be electrically connected to the components 12, 13, 17, 19 of the neural electrode assembly 10 to control each of them or induce them to perform a command.

Figure 3:
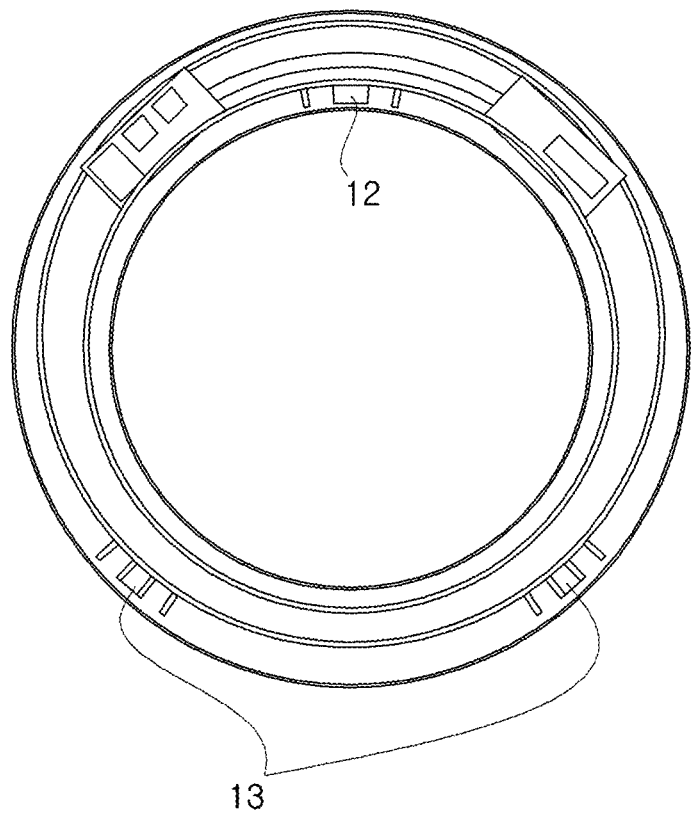
FIG. 3 is a front view of the neural electrode assembly of FIG. 2 according to an embodiment of the present disclosure.

FIG. 3 is a front view of the neural electrode assembly 10 of FIG. 2 according to an embodiment of the present disclosure, and the neural electrode assembly 10 largely includes two types of neural electrodes.

First, the recording neural electrode 12 is disposed around the cervix, and when uterine muscle contraction occurs, detects a corresponding biosignal.

Second, the stimulating neural electrode 13 may stimulate the sympathetic nerves entering the uterus through electrodes disposed in two directions, four o'clock and eight o'clock directions, to suppress the uterine muscle contraction. From the perspective of application, when a contraction-evoked signal is detected in the uterus through the recording neural electrode 12, the stimulating neural electrode 13 may automatically stimulate the nerve entering the uterus, thereby quickly suppressing the uterine contraction.

Figure 4:
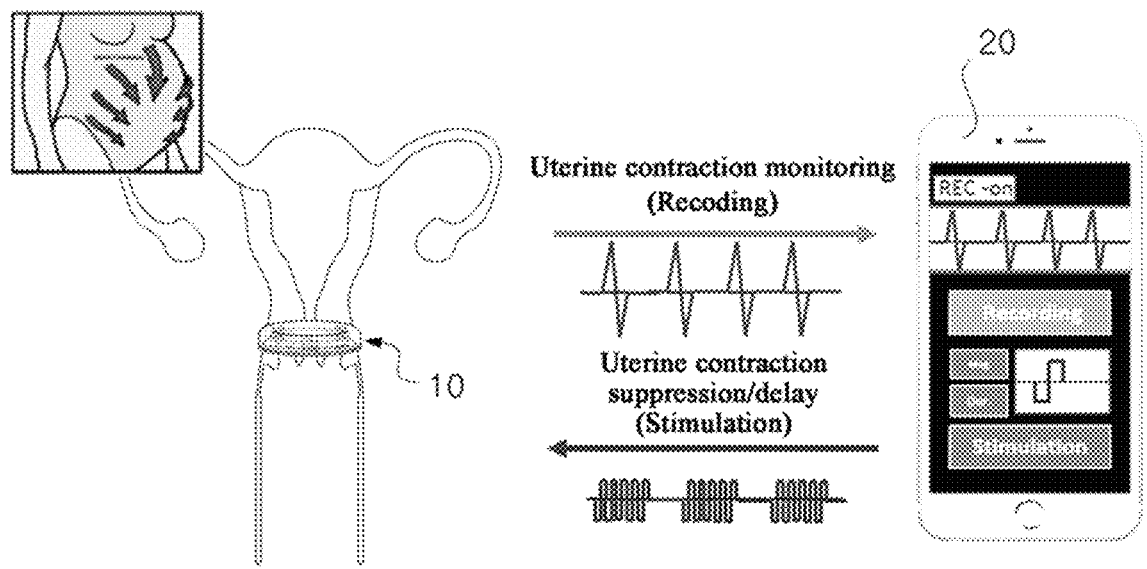
FIG. 4 is a diagram illustrating the operating mechanism of a non-invasive neural electrode control system according to another embodiment of the present disclosure.

FIG. 4 is a diagram illustrating the operating mechanism of a non-invasive neural electrode control system according to another embodiment of the present disclosure.

Preferably, the neural electrode assembly 10 is inserted through the vagina in a non-invasive manner and disposed adjacent to the cervix, and includes an integrated wireless communication module to communicate with the monitoring terminal 20 or a monitoring server outside of the human body. The neural electrode assembly 10 may be worn in, for example, a woman at high risk for preterm birth in 20-25 weeks of pregnancy, and medication may be loaded in part of the body to suppress uterine contractions in conjunction with neural stimulation where necessary.

The monitoring terminal 20 having received a measured uterine muscle contraction signal from the neural electrode assembly 10 disposed at the cervix may diagnose preterm birth through uterine contraction monitoring. For example, the monitoring terminal 20 observes and records the current uterine contraction status in real time through an application program installed therein, and when a uterine muscle contraction beyond the threshold range is detected, the monitoring terminal 20 transmits a command for suppressing or delaying the uterine contraction to the neural electrode assembly 10. Then, the neural electrode assembly 10 suppresses or delays the uterine contraction through electrical stimulation within the allowable range for human body in response to the command, and as a result, prevents preterm birth.

Of course, the application of the nerve stimulation signal for suppressing to uterine contraction may be performed based on the command of the monitoring terminal 20 illustrated through FIG. 4, but may be directly controlled within the neural electrode assembly 10 where required at the time of implementation. In this case, the neural electrode assembly 10 determines if the uterine contraction is in the normal range based on the uterine contraction signal measured itself, and suppresses the uterine contraction by directly stimulating the sympathetic nerves according to the determination result.

Figure 5:
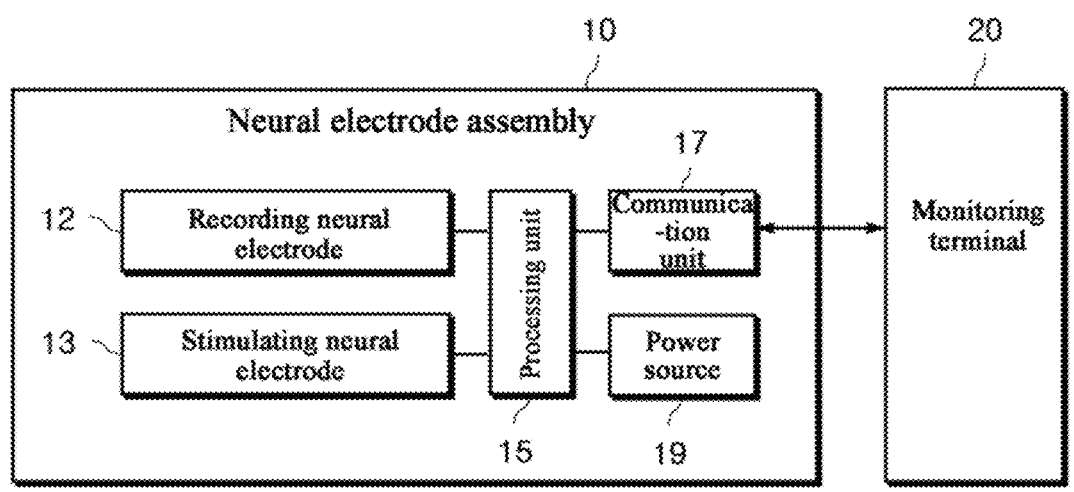
FIG. 5 is a block diagram showing the neural electrode control system of FIG. 4 according to another embodiment of the present disclosure.

FIG. 5 is a block diagram showing the neural electrode control system of FIG. 4 according to another embodiment of the present disclosure, and the outline of each element will be described in brief to avoid redundant descriptions.

The neural electrode assembly 10 that is inserted into the uterus in a non-invasive manner includes the recording neural electrode 12 formed to measure a uterine contraction-evoked neural signal, and the stimulating neural electrode 13 formed to stimulate the nerve entering the uterus to suppress the uterine contraction.

Additionally, the neural electrode assembly 10 may further include the communication unit 17 electrically connected to the recording neural electrode 12 and the stimulating neural electrode 13 to wirelessly transmit and receive a signal and a command. The communication unit 17 transmits the neural signal measured through the recording neural electrode 12 to the monitoring terminal 20, and receives a command for suppressing uterine contraction from the monitoring terminal 20 to induce the control of the stimulating neural electrode 13. The standards of the communication unit implemented through the prototype of the neural electrode assembly are as shown in the following Table 1.

TABLE 1

| Wireless Power Transmission System | |
| --- | --- |
| Coil Diameter | 26.5 mm |
| Input Power | 19 V/200 mA |
| Output Power | 5 V/510 mA |
| Frequency | 125 kHz |
| Max. Distance | 6 mm |

Further, the neural electrode assembly 10 includes the power source 19 to supply power to each component and the processing unit 15 having an integrated algorithm for recording the neural signal or controlling the electrical stimulation. The standards of the power source and the data communication system implemented through the prototype of the neural electrode assembly are as shown in the following Tables 2 and 3.

TABLE 2

| Battery | |
| --- | --- |
| Rated Capacity | 300 mAh @ 3.7 V |
| Charging Condition | 250 mA @ 4.2 V |
| Charging Time | 1~1.2 hour |

TABLE 3

| Wireless Data Communication System | |
| --- | --- |
| Power Consumption | Active: 16 mW |
| | Idle: 3.13 mW |
| | Sleep: 0.95 uW |
| Data Rate | Max. 800 kbps |
| Carrier Frequency | 402~405 MHz |
| Wake-up Frequency | 2.45 GHz |
| Modulation | FSK, bidirectional |

The monitoring terminal 20 communicates with the neural electrode assembly 10, and records, analyzes and visualizes the measured biosignal or transmits the control command for suppressing or delaying uterine contraction.

According to the above-described embodiments of the present disclosure, it is possible to predict or continuously monitor the signs of preterm birth by detecting uterine muscle contractions that are the physiological phenomenon appearing in the mechanism by which preterm birth is induced, and when a uterine contraction is anticipated based on the detected neural signal, automatically apply electrical stimulation to the nerve entering the uterus using the non-invasive neural electrode, to suppress or delay the uterine muscle contraction, thereby preventing preterm birth.

Meanwhile, according to the embodiments of the present disclosure, an algorithm for controlling the non-invasive neural electrode assembly or a series of algorithms for operating the neural electrode control system may be implemented in computer-readable code in a computer-readable recording medium. The computer-readable recording medium includes all types of recording devices in which data that can be read by a computer system is stored.

Examples of the computer-readable recording medium include ROM, RAM, CD-ROM, magnetic tape, floppy disk, and optical data storage devices. Additionally, the computer-readable recording medium is distributed over computer systems connected via a network, and may store and execute the computer-readable code in a distributed manner. Additionally, a functional program, code and a code segment for implementing the present disclosure will be easily inferred by programmers in the technical field to which the present disclosure belongs.

The present disclosure has been hereinabove described with regard to various embodiments. Those skilled in the art will understand that the present disclosure may be embodied in modified form without departing from the essential features of the present disclosure. Therefore, the disclosed embodiments should be considered in descriptive sense rather than in limiting sense. The scope of the present disclosure is defined in the appended claims rather than the foregoing description, and it should be interpreted that the present disclosure covers all differences within the equivalent scope.

DETAILED DESCRIPTION OF MAIN ELEMENTS

10: Neural electrode assembly
11: Body or cover
12: Recording neural electrode
13: Stimulating neural electrode
15: Processing unit
17: Communication unit
19: Power source
20: Monitoring terminal

The invention claimed is:

1. A neural electrode assembly, comprising:
a cover configured to be inserted into a uterus in a non-invasive manner;
a recording neural electrode covered by the cover, and configured to measure a uterine contraction-evoked neural signal; and
a stimulating neural electrode covered by the cover, and configured to stimulate a nerve entering the uterus to suppress a uterine contraction;
wherein
the cover has a ring shape configured to encircle a cervix,
the recording neural electrode is disposed only at an inner part of the cover,
the stimulating neural electrode has two parts disposed only at an outer part of the cover, and
when the recording neural electrode is defined as being positioned at a twelve o'clock position on an inner perimeter of the ring shape, the two parts of the stimulating neural electrode are respectively positioned at a four o'clock position and an eight o'clock position on an outer perimeter of the ring shape, so that when the neural electrode assembly is in place in the uterus, the two parts are respectively adjacent to uterosacral ligaments on sides of the cervix.

2. The neural electrode assembly according to claim 1, wherein the recording neural electrode is configured to be disposed around the cervix by the insertion of the cover into the uterus, to continuously monitor the uterine contraction-evoked neural signal.

3. The neural electrode assembly according to claim 1, wherein the stimulating neural electrode is configured to stimulate the nerve entering the uterus to suppress the uterine contraction, when the uterine contraction is detected through the recording neural electrode.

4. The neural electrode assembly according to claim 3, wherein the stimulating neural electrode is configured to apply, to the nerve entering the uterus, a nerve stimulation signal of sufficient intensity to stop or delay preterm birth, corresponding to a detected degree of uterine contraction.

5. The neural electrode assembly according to claim 1, wherein the stimulating neural electrode is configured to stimulate sympathetic nerves of the uterosacral ligaments to suppress the uterine contraction.

6. The neural electrode assembly according to claim 1, wherein the cover includes at least one biocompatible material of ethylene vinyl acetate (EVA) copolymer, poly ethylene (PE), poly styrene (PS), poly ethylene terephthalate (PET), poly vinyl chloride (PVC), poly vinylidene chloride (PVDC), poly propylene (PP), and poly vinyl alcohol (PVA).

7. The neural electrode assembly according to claim 1, further comprising:
a communication unit electrically connected to the recording neural electrode and the stimulating neural electrode to wirelessly transmit and receive a signal and a command,
wherein the communication unit is configured to:
transmit the neural signal measured through the recording neural electrode to a monitoring terminal, and
receive a command for suppressing the uterine contraction from the monitoring terminal to control the stimulating neural electrode.

8. The neural electrode assembly according to claim 7, wherein
the cover has an upper part and a lower part; and
the recording neural electrode, the stimulating neural electrode and the communication unit are ring-shaped and configured to be accommodated between the upper part and the lower part of the cover.

9. The neural electrode assembly according to claim 8, wherein the ring-shaped recording neural electrode and stimulating neural electrode are concentric, the stimulating neural electrode being outside of the recording neural electrode.

10. The neural electrode assembly according to claim 9, further comprising a power source and a processing unit contained within the cover, the power source being configured to supply power to the neural electrode assembly, and the processing unit being electrically connected to each of the recording neural electrode, the stimulating electrode, the communication unit and the power source, to control each of the recording neural electrode, the stimulating electrode, the communication unit and the power source.

11. The neural electrode assembly according to claim 10, wherein in a plan view the power source and the processing unit are disposed between the recording neural electrode and the stimulating electrode, and overlap the communication unit.

12. A neural electrode control system, comprising:
a neural electrode assembly that is configured to be inserted into a uterus in a non-invasive manner to continuously measure a uterine contraction-evoked neural signal and stimulate a nerve entering the uterus to suppress a uterine contraction; and
a monitoring terminal to receive the uterine contraction-evoked neural signal continuously measured through the neural electrode assembly, and when the uterine contraction is detected, transmit a command for suppressing the uterine contraction to the neural electrode assembly to induce the neural electrode assembly to stimulate the nerve entering the uterus;
wherein the neural electrode assembly includes:
a recording neural electrode configured to be disposed around a cervix by the insertion into the uterus, to continuously monitor the uterine contraction-evoked neural signal;
a stimulating neural electrode configured to be disposed adjacent to uterosacral ligaments on both sides of the cervix by the insertion into the uterus, to stimulate sympathetic nerves of the uterosacral ligaments to suppress the uterine contraction; and
a cover having a ring shape, the cover covering the recording neural electrode and stimulating neural electrode, and configured to encircle the cervix; and
wherein
the recording neural electrode is disposed only at an inner part of the cover,
the stimulating neural electrode has two parts disposed only at an outer part of the cover, and
when the recording neural electrode is defined as being positioned at a twelve o'clock position on an inner perimeter of the ring shape, the two parts of the stimulating neural electrode are respectively positioned at a four o'clock position and an eight o'clock position on an outer perimeter of the ring shape, so that when the neural electrode assembly is in place in the uterus, the two parts are respectively adjacent to uterosacral ligaments on sides of the cervix.

* * * * *